Figure 1:
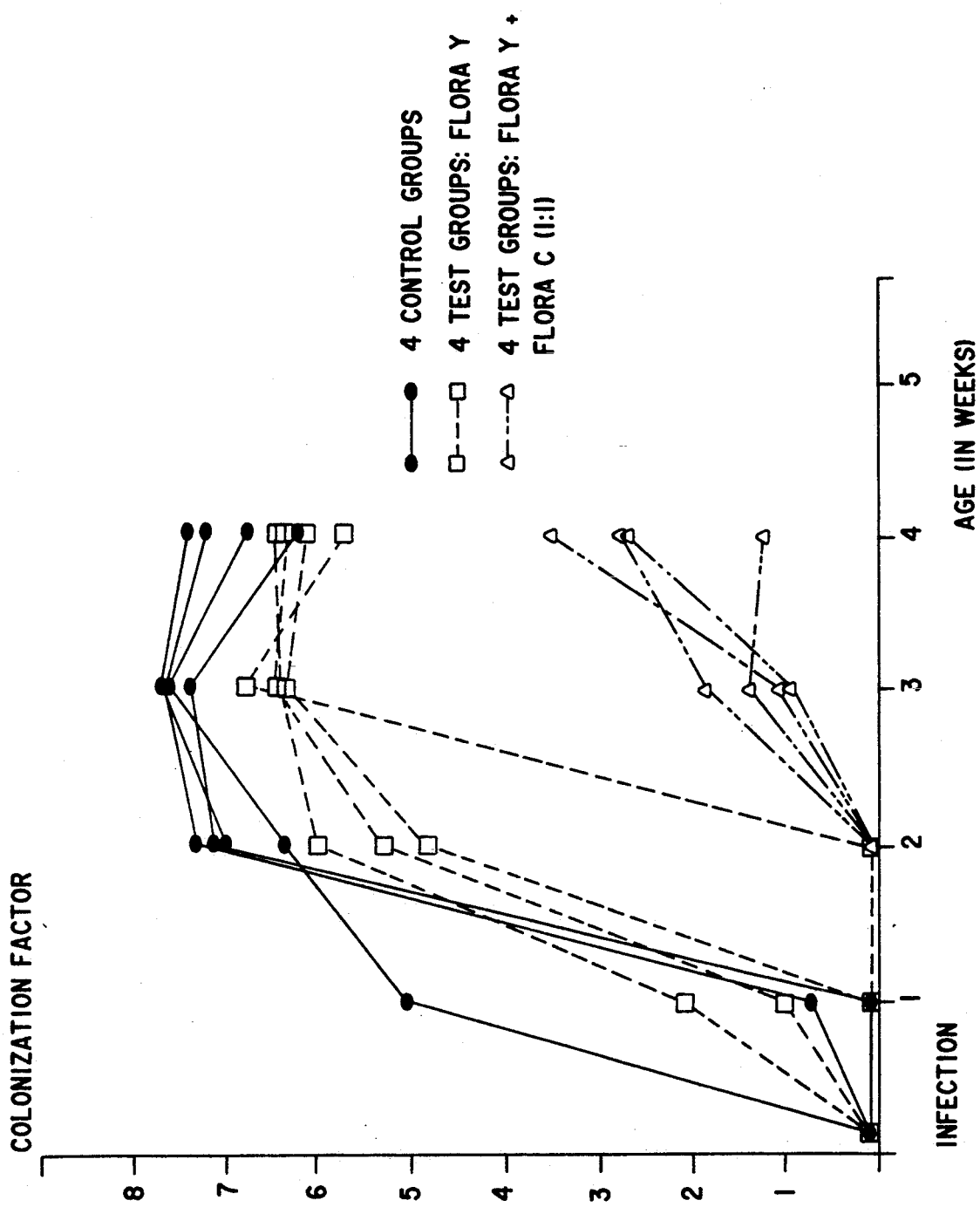

United States Patent [19]

Nuotio et al.

[11] Patent Number: 5,252,329

[45] Date of Patent: Oct. 12, 1993

[54] BACTERIAL PREPARATION FOR USE IN POULTRY

[75] Inventors: Lasse O. Nuotio, Imatra; Matti A. Aho; Esko V. Nurmi, both of Helsinki, all of Finland

[73] Assignee: Orion-Yhtyma OY, Turku, Finland

[21] Appl. No.: 777,539

[22] PCT Filed: Jun. 27, 1990

[86] PCT No.: PCT/FI90/00171

§ 371 Date: Dec. 9, 1991

§ 102(e) Date: Dec. 9, 1991

[87] PCT Pub. No.: WO91/00099

PCT Pub. Date: Jan. 10, 1991

[30] Foreign Application Priority Data

Jun. 30, 1989 [GB] United Kingdom ................ 8915027

[51] Int. Cl.$^5$ .............................................. C12N 1/20
[52] U.S. Cl. ........................................ 424/93 C; 426/2
[58] Field of Search ......................... 424/93 C; 426/2

[56] References Cited

FOREIGN PATENT DOCUMENTS 0006695 1/1980 European Pat. Off. .
0033584 8/1981 European Pat. Off. .
0154478 9/1985 European Pat. Off. .

OTHER PUBLICATIONS

Rosende et al., Advances en Ciencias Veterinarias 1(1): 26–29 1986.
Poultry Science 1988, 67(7) 1026–1033.
Journal Hygiene 1982, 26(3), 521–524.
Avian Diseases 1982, 26(3), 521–524.
Canadian J. Microbiology 1985, 31(9), 832–838.
Veterinary Quarterly 1984 6(2), 73–79.
Food Microbiology 1984, 1, 143–147.
Avian Diseases 1983, 28(1), 139–146.
Epidem. Inf. 1988, 100, 27–34.

Primary Examiner—Douglas W. Robinson
Assistant Examiner—Jean C. Witz
Attorney, Agent, or Firm—Armstrong, Westerman, Hattori, McLeland & Naughton

[57] ABSTRACT

A bacterial preparation useful for the prophylaxis of intestinal bacterial infections, especially Campylobacter infections, in poultry comprises bacteria derived from an adult bird from the same microecological niche, especially in the caecum, where the pathogenic bacteria tend to propagate in newly hatched chickens.

2 Claims, 2 Drawing Sheets

BACTERIAL PREPARATION FOR USE IN POULTRY

This invention relates to a bacterial preparation for use in poultry, especially for the prevention of colonization of the gut by human pathogenic bacteria, particularly Campylobacter spp.

Poultry is the most important source of human campylobacter and salmonella infections. The role of *Campylobacter jejuni* and *Campylobacter coli* as common causes of human gastrointestinal diseases is well documented. The reference King, E. O.: "The laboratory recognition of Vibrio fetus and a closely related Vibrio isolated from cases of human vibrosis", Annals of the New York Academy of Sciences, 98:700–711, 1962 proposed chickens as the primary source of human infections. Skirrow, M. B.: "Campylobacter enteritis: a 'new' disease", Brit. Med. J. 2:9–11 (1977) demonstrated an association in some cases between human disease and contact with chickens carrying the organism on farms, in butcher shops and in home kitchens. This association was later documented in several epidemiological studies, e.g. Harris, N. V., Weiss, N. S. and Nolan C. M.: "The role of poultry and meats in the etiology of *Campylobacter jejuni* coli enteritis". Am. J. of Public Health 76:407–411 (1986). There are also several reports of outbreaks in which the epidemiologically implicated or suspected vehicle of campylobacteriosis has been raw, barbecued or undercooked chicken. According to Newsletter no 20 published by WHO in April 1989 the number of campylobacter infections has exceeded the number of salmonella infections in the last years in several industrialized countries.

In a study, carried out at the National Veterinary Institute in Finland, it was confirmed that a probable reason for susceptibility of broilers to salmonella colonization (growth and attachment) in the intestines was the delayed development of the normal intestinal bacterial flora. This delay is a result of the modern mass-breeding methods of raising broilers. Such animals have therefore a low defence against exogenous bacteria entering the body. E. Nurmi and M. Rantala, Nature 241:210–211, 1973 demonstrated that normal adult gut contents given to newly hatched chicks increased their resistance to salmonella colonization. Based on this pioneer work the theory of competitive exclusion (in the following CE) was formulated. Bacterial preparations especially for the prophylaxis of salmonella infections in poultry have been disclosed, e.g. in EP 6695, EP 33584 and EP 154478. The success in preventing Salmonella by competitive exclusion in broiler chicks has encouraged several working groups around the world to apply the same method for the prophylaxis of Campylobacter ssp. Soerjadi-Lien, Snoeyenbos and Weinack, Avian Diseases 26:520–(1982) and 28:139–(1983) have reported that when a 10% suspension of faeces from specific pathogen free (SPF) flocks colonized with an optimally protective microflora was administered to young chicks their resistance to *C. jejuni* increased. This research team further reported that the CE-effect of an administered microflora diminished with increasing doses of Campylobacter spp. According to other reports of CE on Campylobacter spp. no effect was found either by using CE-floras generated from faecal and caecal excreta (Stern, Bailey and Blankenship, Avian Diseases 32:330–334, 1988) or by using CE-floras generated from fresh adult caecal flora (Shanker, Lee & Sorrel, Epidemiology and Infection 100:27–34, 1988).

The present invention provides a bacterial preparation useful for the prophylaxis of colonization of human pathogenic bacteria in poultry comprising bacteria derived from an adult bird, from the microecological niche which pathogenic bacteria occupy.

The preparation of this invention comprises a bacteria flora, derived more particularly from the normal caecal flora and especially the caecal mucous layer of adult birds, which may be used for inhibiting the colonization of human pathogenic bacteria, especially Campylobacter, in young birds. The results reported herein disclose the reduction of the colonization of *C. jejuni* biotype 1 in broiler chicks. The bacterial preparation of the invention also is effective against other Campylobacter species and possibly also other pathogenic bacteria.

The flora used in the present invention is selected from the same microecological niche which Campylobacteria tend to occupy in the cecum of broiler chickens. Highly effective floras are obtained by culturing the bacterial flora from the mucous layer of the caecal wall from an adult bird under either anaerobic or microaerophilic conditions, preferably in a mucin broth. It is also preferable to select bacteria with high motility in mucin.

The floras used in the experiments were all generated from the caecum of an older, egg-laying hen.

GENERATION OF THE FLORAS

Caecal homogenate (Flora A)

The whole caecum was homogenized and diluted with 0.1% peptone water in laboratory scale experiments and normal potable water in farm scale experiments. The flora contained no Salmonella spp. or Campylobacter spp. The test methods were the following:

| | |
|---|---|
| Salmonella: | 1% buffered peptone water (37° C./20 h), Rappaport-Vassiliadis broth 41.5° C./20 h) and tetrathionate broth (37° C./20 h), Onöz and brilliant green agars (37° C./20 h) |
| Campylobacter: | Brucella Broth supplemented with pyruvate, metabisulfite and ferrous iron (FBP) (41.5° C./20 h in microaerophilic atmosphere), CCD agar (41.5° C./44 h in microaerophilic atmosphere) |

Cultured caecal homogenate (Flora B)

1 ml of caecal homogenate was used to inoculate 100 ml of Brucella Broth (BBL) reinforced with 1 g of Porcine Gastric Mucin (SIGMA). Mucin was suspended in small portions into boiling water and neutralized before adding to the rest of the medium. Cefoperazone (Cefobis, Pfizer) was added aseptically after autoclaving to a final concentration of 32 mg/l. The incubation was continued for 48 h at 41.5° C. under microaerophilic conditions.

Purified cultured caecal mucous layer (Flora C)

The essential part of nonmotile bacteria of flora B were discharged by semisolid 10% mucin agar which have the following composition

| Semisolid 10% mucin agar: | |
|---|---|
| Mucin | 10.00 g |
| Brucella broth | 0.50 g |

-continued

| Semisolid 10% mucin agar: | |
|---|---|
| $K_2HPO_4$ | 0.25 g |
| Agar | 1.10 g |
| Water | 100 ml |

Mucin must be dissolved in boiling water befor autoclaving. pH is adjusted to 7.2 with 0.1 N NaOH.

The flora B was transferred in a line on a 12 cm petri dish containing 33 ml of semisolid 10% mucin agar.

After microaerophilic incubation (41.5° C./48 h/oxygen 5%, $CO_2$ 15% and nitrogen 80%) a small amount of agar between 2 and 4 cm of the line was transferred to a 10% mucin broth. The composition of this broth was the same as the 10% mucin agar except that it contained no cefoperazone and no agar. The procedure was repeated until no nonmotile bacteria were observed in the broth.

Isolation of the bacteria

Flora C was cultured on Brucella agar and in microaerophilic atmosphere at 41.5° C. for from 48 to 96 h. Motile spiral shaped organisms were isolated.

Flora B was transferred in a line on a 12 cm petri dish containing 33 ml of semisolid 10% mucin agar. After anaerobic incubation (41.5° C./48 h), a small amount of agar from 2 to 4 cm off the line was transferred to 10% mucin broth II which was also incubated in an anaerobic atmosphere. This procedure was repeated until no nonmotile bacteria were detected in the broth. After three repeats there was only one kind of bacteria denoted Y left in the broth.

ADMINISTRATION OF THE FLORAS

Laboratory Trials

In the laboratory trials 60-72 newly hatched chicks were divided into 12 groups. The CE-floras were administered into the crops of the birds of 2×4 groups. The remaining four groups were used as controls, and they received no CE-floras. The next day 1000-3000 CFU of *C. jejuni* biotype I Penner 15 or Penner 3/43/59, was given by the same method to all groups except two of the four control groups. Half of the birds were killed after one week and the rest after two weeks. Quantitative examination of Campylobacteria was carried out from the caeca of the birds.

Field Trials

In the field trials 1600-1700 chickens were divided into 16 groups, eight of which served as test groups, four as Campylobacter positive control groups and four as reference groups. CE-floras were mixed into the first drinking water of eight test groups. 4.16-5.80 $\log_{10}$ CFU of *C. jejuni* biotype 1 Penner 15 was administered the next day to three seeder birds in each cage except in the cages of four reference groups. Each week until the end of the growing period three to five birds were killed from each cage and the caeca were examined quantitatively for Campylobacter spp.

Brucella broth with FBP (ferrous sulfate, sodium metabisulfite and sodium pyruvate each 0.5 g/l) and cefoperazone (32 mg/l) and Charcoal-Cefoperazone-Deoxychloate (CCD) agar were used in qualitative and quantitative examinations of campylobacter spp. Broths were incubated for 20 h and agars for 44 h at 41.5° C. in a microaerophilic atmosphere.

Results

The colonization factor is the arithmetic mean value of the $\log_{10}$-values of the number of CFU per g of caecal content of the individual birds, in each test or control group.

A campylobacter negative (both in quantitative and in qualitative examination) bird by convention has a $\log_{10}$-value of 0.1 in the calculations.

EXPERIMENT 1

Laboratory Trials

Table 1 shows that microaerophilic incubation of flora B provided more effective competitive exclusion of Campylobacter spp than anaerobic incubation of flora B.

TABLE 1

| Challenge dose 895 CFU of *C. jejuni* biotype I heat stable serotype 15/chicken | | |
|---|---|---|
| | Colonization factor | |
| | 1 week | 2 weeks |
| Control 1 | 5.13 | 7.74 |
| Control 2 | 5.96 | 8.35 |
| Flora B microaerophilic culture | | |
| Group 1 | <2.00 | <2.00 |
| Group 2 | <2.00 | <2.00 |
| Group 3 | <2.00 | <2.00 |
| Group 4 | 2.34 | <2.00 |
| Flora B anaerobic Culture | | |
| Group | <2.00 | 3.24 |
| Group 2 | 4.91 | <2.00 |
| Group 3 | 3.89 | <2.00 |
| Group 4 | 3.70 | 7.04 |

EXPERIMENT 2

Flora B was purified according to motility and atmosphere into a microaerophilic flora C and an anaerobic bacteria flora Y as described above. The anaerobic bacteria Y alone did not evoke the CE-effect. The combination of these floras (1:1) returned the CE-effect as shown in groups 3 and 4, table 2.

Laboratory Trials

TABLE 2

| Challenge dose 245 CFU of *C. jejuni* biotype I heat-stable serotype 15/chicken | | |
|---|---|---|
| | Colonization factor | |
| | 1 week | 2 weeks |
| Control 1 | 7.78 | 7.58 |
| Control 2 | 8.33 | 8.74 |
| Flora Y alone | | |
| Group 1 | 1.90 | 6.70 |
| Group 2 | 6.55 | 8.06 |
| Flora Y + Flora C (1:1) | | |
| Group 3 | 1.80 | <2.00 |
| Group 4 | 3.22 | <2.00 |

Field Trials

16×100 broiler chickens were grown in a normal growing unit for six weeks. Eight groups were used in a competitive exclusion experiment. Four groups served as a negative control, not shown in the picture. The test groups were given two kinds of specified caecal floras in their first drinking water. Dilutions of the floras were 1/30. Each bird received approximately 0.25 ml of treatment liquid.

Four test groups were given mucin adapted anaerobic motile bacteria (flora Y). The remaining four groups received combined flora (1:1) consisting of flora Y and flora C, which is a mucin adapted microaerophilic flora as described above.

36 broiler chickens were infected with *Campylobacter jejuni* biotype 1, Penner serotype 15 at the age of one day. The dose was $\log_{10} 4.16$ CFU. Three of these seeders were delivered to each group.

Caecal contents of three birds from each group were examined quantitatively at weekly intervals for Campylocateria on CCD-agars. The colonization factor was calculated as an arithmetic average of the $\log_{10}$-values of the number of CFU per gram of caecal content of the individual birds in each group. Negative control remained qualitatively negative for Campylobacter spp. until slaughter.

The results are shown in FIG. 1. It can be seen that mucin adapted anaerobic motile bacteria (flora Y) did not protect the caeca from the colonization of campylobacter spp. although the number of campylobacter spp. in caeca decreased slightly (by $<1$ $\log_{10}$-unit). Combination (1:1) of flora Y and flora C delayed the beginning of the colonization of campylobacter spp. by 2 weeks. After 3 weeks of the infection the number of campylobacter spp. remained at a level of 4 $\log_{10}$-units lower than in the control groups.

EXPERIMENT 3

The CE effect of a diluted homogenate of the caecum (flora A) was compared with the CE effect of an unspecified caecal flora grown in an anaerobic atmosphere. The amount of tested birds and groups as well as the amount of administered CE-flora per bird were the same as in the foregoing experiment. Four test groups got flora A and four groups got an unspecified caecal flora grown in anaerobic atmosphere. This flora is called 427/C. Eighteen broiler chickens were infected with *Campylobacter jejuni* biotype 1, Penner serotype 15 at the age of 18 days. Dose was $\log_{10} 5.80$ CFU. Three of these seeders were delivered to each group.

Figure 2:
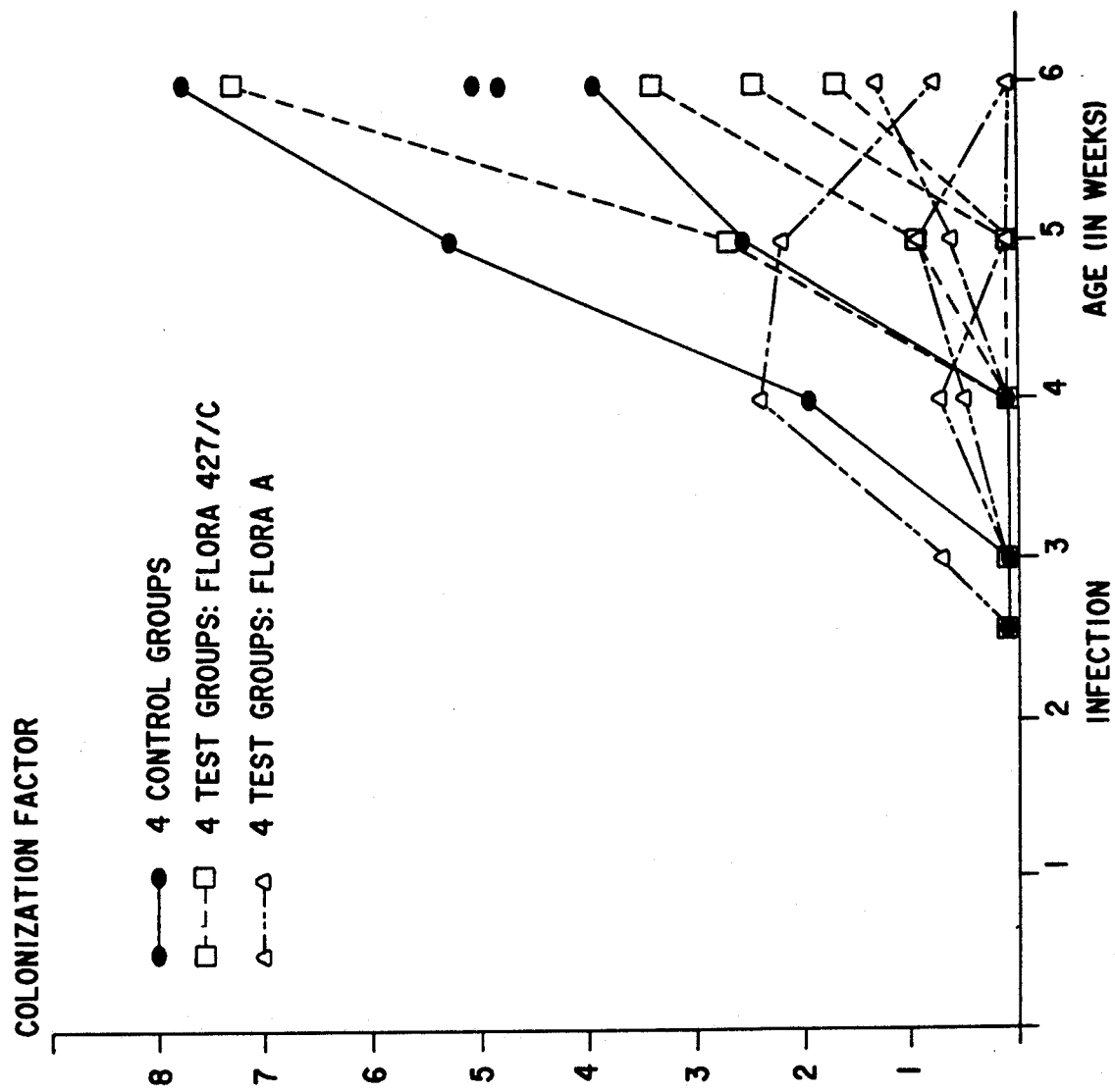

FIG. 2 shows that flora A (the diluted homogenate of the caecum) showed the more efficient CE effect.

Flora A apparently colonized the caeca of the chickens and prevented colonization of *C. jejuni* in two groups and decreased the rate of colonization (by 4 $\log_{10}$-units) in the other two groups. Flora 427/C delays the beginning of the infection by 1–2 weeks but probably after two weeks the number of Campylobacteria in the caeca of the chickens would be at the same level as in the caeca of the control groups (fully colonized by Campylobacter spp.).

We claim:

1. A bacterial composition having a competitive exclusion effect on Campylobacteria and being useful for the prophylaxis of Campylobacter spp. infections in poultry, comprising a composition obtained by culturing bacteria, derived from the mucous layer of the caecum of an adult bird in a mucin broth under microaerophillic conditions and isolating spiral shaped motile bacteria from the mucin broth.

2. A process for producing a bacterial composition having a competitive exclusion effect on Campylobacteria and being useful for the prophylaxis of Campylobacter spp. infections in poultry, which process comprises culturing bacteria derived from the mucous layer of the caecum of an adult bird in a mucin broth under microaerophilic conditions and isolating spiral shaped motile bacteria from the mucin broth.

* * * * *